United States Patent [19]

So et al.

[11] Patent Number: 5,441,699

[45] Date of Patent: Aug. 15, 1995

[54] APPARATUS FOR AUTOMATICALLY ANALYZING LIQUID TEST SAMPLES

[75] Inventors: Jai-Choon So; Hae-Il Kwak; Kyu-Hae Kwang; Yong-Hwan Cho; Ki-Jin Eom; Sa-Ryong Pack, all of Pohang, Rep. of Korea

[73] Assignees: Pohang Iron & Steel Co., Ltd.; Research Institute of Industrial Science & Technology, both of Kyong Sang Book-Do, Rep. of Korea

[21] Appl. No.: 174,144

[22] Filed: Dec. 28, 1993

[30] Foreign Application Priority Data

Dec. 28, 1992 [KR] Rep. of Korea ............... 1992-25813
Dec. 29, 1992 [KR] Rep. of Korea ............... 1992-25993
Dec. 30, 1992 [KR] Rep. of Korea ......... 1992-27641 U
Dec. 16, 1993 [KR] Rep. of Korea ............... 1993-27975

[51] Int. Cl.⁶ .................... G01N 35/10; G01N 35/00
[52] U.S. Cl. ........................ 422/63; 422/65; 422/67; 422/81; 422/100; 422/101; 436/43; 436/44; 436/47; 436/48; 436/177; 436/180
[58] Field of Search ............. 422/63, 65, 66, 67, 422/81, 100, 101; 436/43, 44, 46, 47, 48, 49, 54, 180, 177

[56] References Cited

U.S. PATENT DOCUMENTS

| | | | |
|---|---|---|---|
| 4,058,367 | 11/1977 | Gilford | 422/63 |
| 4,095,472 | 6/1978 | Mowery, Jr. | 73/422 |
| 4,168,955 | 9/1979 | Allington | 422/65 |
| 4,269,803 | 5/1981 | Jessop | 422/63 |
| 4,710,352 | 12/1987 | Slater et al. | 422/63 |
| 4,876,204 | 10/1989 | Inoue et al. | 436/46 |
| 4,876,926 | 10/1989 | Muszak | 81/3.2 |
| 4,943,416 | 7/1990 | Kikuchi et al. | 422/63 |
| 5,122,342 | 6/1992 | McCulloch et al. | 422/65 |
| 5,209,903 | 5/1993 | Kanamori et al. | 422/65 |

*Primary Examiner*—James C. Housel
*Assistant Examiner*—Long V. Le
*Attorney, Agent, or Firm*—Webb Ziesenheim Bruening Logsdon Orkin & Hanson

[57] ABSTRACT

An apparatus for automatically analyzing various solutions which are used in the production lines of various industrial fields. Particularly, in the case where the ingredients of a solution is to be analyzed, the test sample is taken in an automatic manner, and carried over a long distance. The carried test sample is subjected to an automatic pre-treatment and an automatic ingredient analysis. Thus the ingredients of a solution can be analyzed in a speedy and accurate manner. Further, the results of the analysis are treated with an on-line real time to be fed back in a speedy manner, and therefore, it is made possible to strictly control the solution ingredients, thereby contributing to the improvement of the quality of products. Furthermore, the expensive analyzing instruments can be protected from corrosion.

11 Claims, 14 Drawing Sheets

(B)

APPARATUS FOR AUTOMATICALLY ANALYZING LIQUID TEST SAMPLES

FIELD OF THE INVENTION

The present invention relates to an apparatus for automatically analyzing various solutions used in various industrial fields. In particular, the present invention relates to an apparatus for automatically analyzing liquid test samples, in which, when analyzing the ingredients of a liquid test sample, the test sample can be automatically taken, it can be carried over a long distance, and the whole process including the pre-treatment to the final composition analysis can be automatically carried out, whereby the ingredient elements of the liquid test sample can be measured in an accurate and speedy manner.

BACKGROUND OF THE INVENTION

Generally, when various solutions which are used in the manufacturing process of various industrial fields are to be subjected to an ingredient analysis for the purpose of quality control, a certain amount of a particular solution is sampled, and carried to the place where the analyzing apparatus is located. Then the solution sample which has been thus carried is subjected to a pre-treatment so as for the sample to be suitable for analysis. Then the analyzing apparatus carries out a quantitative analysis. Thus the automatic analyzing apparatus refers to such a wholly automatic analyzing apparatus. In the currently used conventional apparatus for analyzing liquid test samples, a pipe connects from the container of the solution to the place where the analyzing apparatus is located. Further, a pump is installed at an intermediate position on the pipe for pumping the test sample of the solution to the destination. Then a proper amount of the sample is taken out, and a pre-treatment is carried out so as for it to be suitable for the analysis, before carrying out the final analysis.

FIG. 13 illustrates a conventional automatic liquid sample analyzing apparatus 1000. As shown in this drawing, a pump 1014 is connected through a tube 1012 to an electroplating tank 1010 which contains an electroplating electrolyte P. The pump 1014 is provided with a discharge tube 1016 which is connected to a test sample diluting container 1020 which is installed within the liquid sample analyzing apparatus 1000. Adjacently to the test sample diluting container 1020, there is located a test sample taking container 1022 which is connected to the container 1020 through a tube 1026. The test sample taking container 1022 is further connected through a tube 1028 to a test sample taking unit 1030. At a side of the test sample taking unit 1030, there is a droplet filter paper storing unit 1032, and, below it, there is a circular supporting table 1036 upon which a droplet filtering paper 1034 is mounted, the droplet filter 1034 being rotatably supported by a motor (not shown). At the opposite side of the droplet filter storing unit 1032, there is installed a dryer 1038, while, a conveyor device 1040 is below the circular supporting table 1036.

In the above described conventional automatic liquid test sample analyzing apparatus 1000, first, a certain amount of the electroplating electrolyte P is transferred by the pump 1014 through the tubes 1012 and 1016 to the test sample diluting container 1020. In the test sample diluting container 1020, a distilled water supplied through the tube 1017 and the electrolyte p are mixed together so as to be diluted. After the dilution, the electrolyte P is transferred through the tube 1026 to the test sample taking container 1022, and, at the same time, the droplet filtering paper 1034 is supplied from the droplet filter storing unit 1032 into a hole of the circular supporting table 1036. At the same time, the circular supporting table 1036 is rotated driven by the motor, so that the filtering paper 1034 should be positioned below the test sample taking unit 1030. Under this condition, the test sample taking unit 1030 takes a certain amount of test sample solution to drop it onto the droplet filtering paper 1034 which is placed on the circular supporting table 1036. Thus when the dropping of the test sample solution onto the droplet filtering paper 1034 is completed, the circular supporting table 1036 is rotated by 90° driven by the motor. Under this condition, the dryer 1038 dries the relevant droplet filtering paper 1034, and, after the completion of the drying, the circular supporting table 1036 is rotated by 90° again, so that the droplet filtering paper 1034 should be dropped down. Then the droplet filtering paper 1034 is conveyed by the conveyor 1040 to the place where a fluorescent X-ray analyzer is located.

Now the method of treating the filtering paper will be described referring to FIG. 12.

A paraffin 1054 is applied on a filtering paper 1050 by means of a stamp 1052 to form an annular ring having a diameter (e.g., 360 mm). Then by using a micro pipette 1056, a certain amount of the test sample solution is dropped within the annular paraffin 1054. Then the test sample solution is dried, and is put into a test sample container 1059 after cutting the filtering paper.

However, in the conventional automatic liquid test sample analyzing apparatus 1000, a long distance transportation of the test sample is impossible. Further, the test sample does not circulate, and therefore, the test sample is stagnated within the discharge tube. Therefore, in the case where the production is continued, there is generated a difference between the electrolyte of the electroplating tank 1010 and the test sample remaining within the tube. Therefore, when the composition and physical properties of the test sample thus obtained are measured, the test results are different from the properties of the solution within the electroplating tank 1010, with the result that there occurs problem in the quality control. Particularly, in the case where potassium chloride (KCl) is contained in an over-saturation state as in the case of electroplating electrolyte P, the temperature of the solution drops during carriage through the tube, and there occurs frequently the blocking of the tube due to the precipitation of certain ingredients. Further, the conventional apparatus 1000 is installed near the solution tank (electroplating tank), and therefore, in the case where the test sample is an acid solution having a strong corroding action like the electroplating electrolyte, the expensive precision measuring instrument is corroded and put to disorders. In the case where the test sample includes various kinds, the sample taking and analyzing apparatuses have to be installed adjacently to the storing tanks due to the impossibility of a long distance transportation of the test samples, with the result that overlapping investments have to be made in the expensive apparatuses.

SUMMARY OF THE INVENTION

The present invention is intended to overcome the above described disadvantages of the conventional techniques.

Therefore it is the object of the present invention to provide an apparatus for automatically analyzing liquid test samples, in which the tubes are not blocked by the solutions, the generation of the differences of the ingredients within the tube is prevented, the expensive analyzing instruments are not subjected to corrosion even under a severely corroding atmosphere by performing the tests after carrying the test sample to an analyzing room, and the test results for the liquid test samples are subjected to an on-line real time processing to feed back the results in a speedy manner, whereby the solution is managed in a strict manner, and the quality of the products can be improved.

In achieving the above object, the apparatus according to the present invention includes:

- a test sample taking section for taking samples from a solution tank to put them into a sampling bottle;
- a test sample carrying section for carrying the sampling bottle containing the test sample after taking the sample from the solution tank;
- a test sample readying section for opening the cap of the sampling bottle to draw the sample from the bottle;
- a test sample pre-treating section for diluting the sample, for adding particular ingredients or for extracting particular ingredients after drawing the sample by the sample readying section;
- a filtered test sample preparing section for processing the liquid test sample of the sample pre-treating section based on a filtering method; and
- an analyzer for analyzing the ingredients of the test sample supplied from the test sample pre-treating section and the filtered sample preparing section.

BRIEF DESCRIPTION OF THE DRAWINGS

The above object and other advantages of the present invention will become more apparent by describing in detail the preferred embodiment of the present invention with reference to the attached drawings in which.

DESCRIPTION OF THE PREFERRED EMBODIMENT

Figure 1:
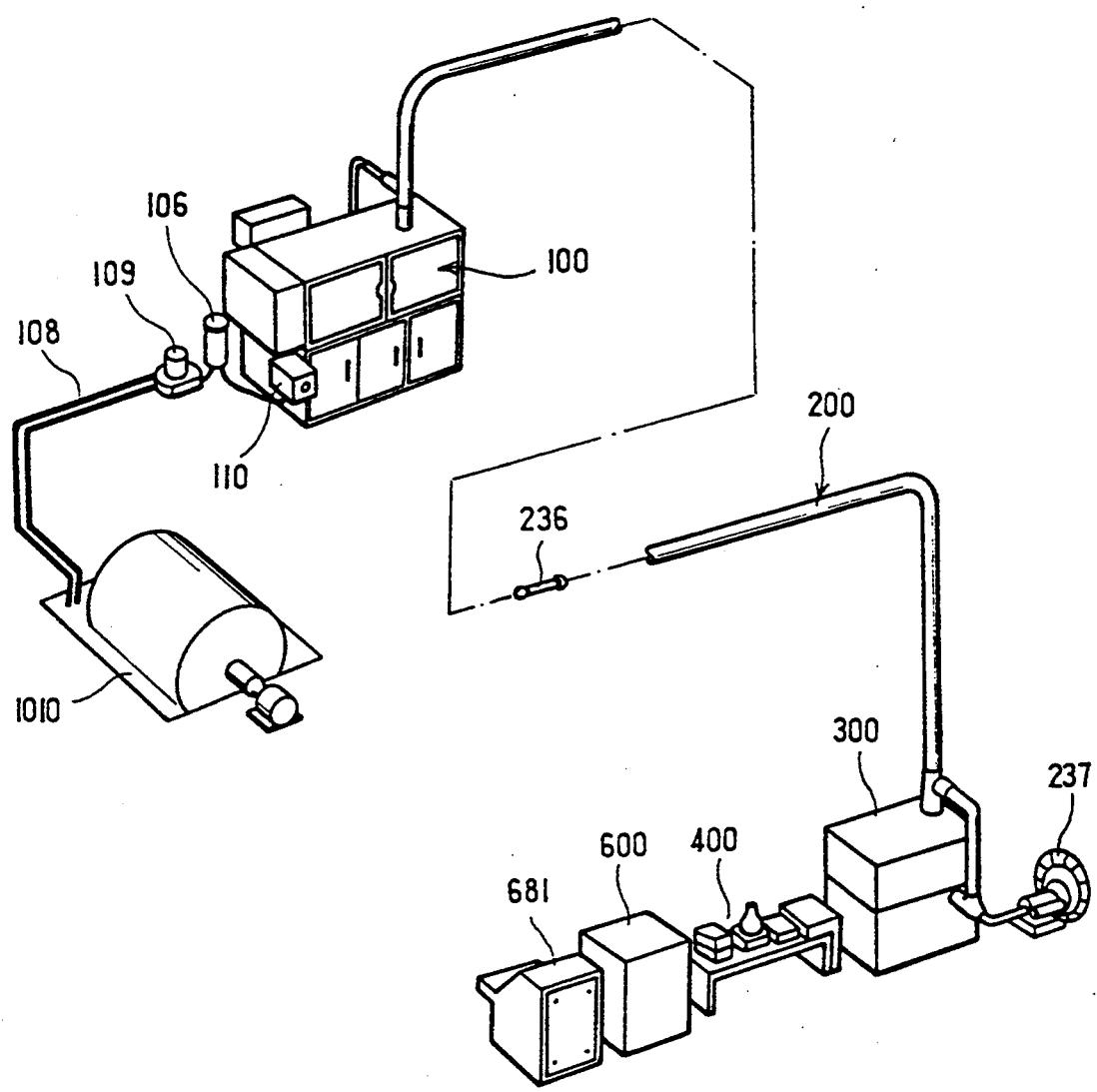
FIG. 1 is a schematic view showing the total constitution of the apparatus according to the present invention.
Figure 2:
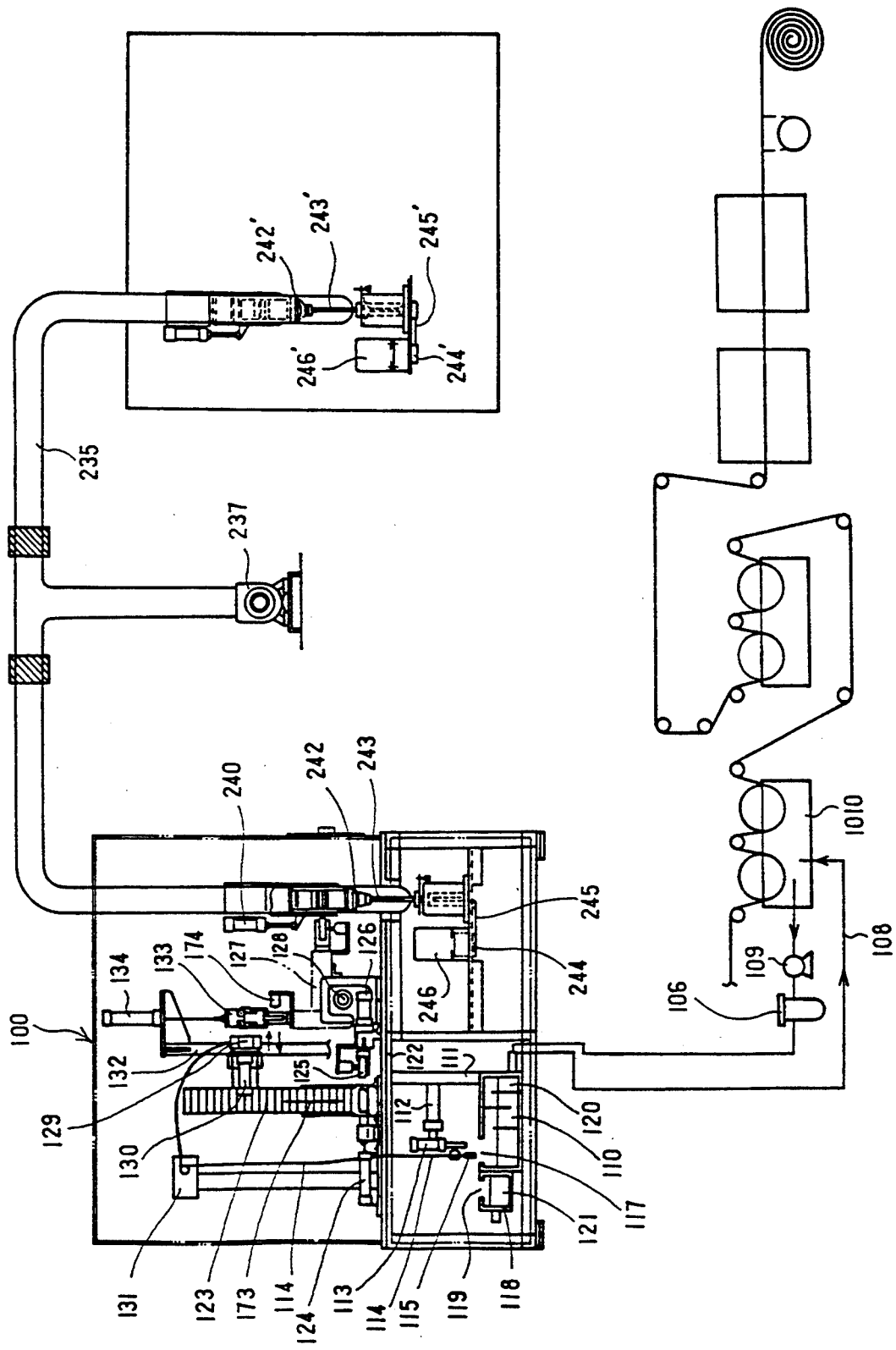
FIG. 2 illustrates the constitutions of the test sample taking section and the test sample carrying section according to the present invention.
Figure 3:
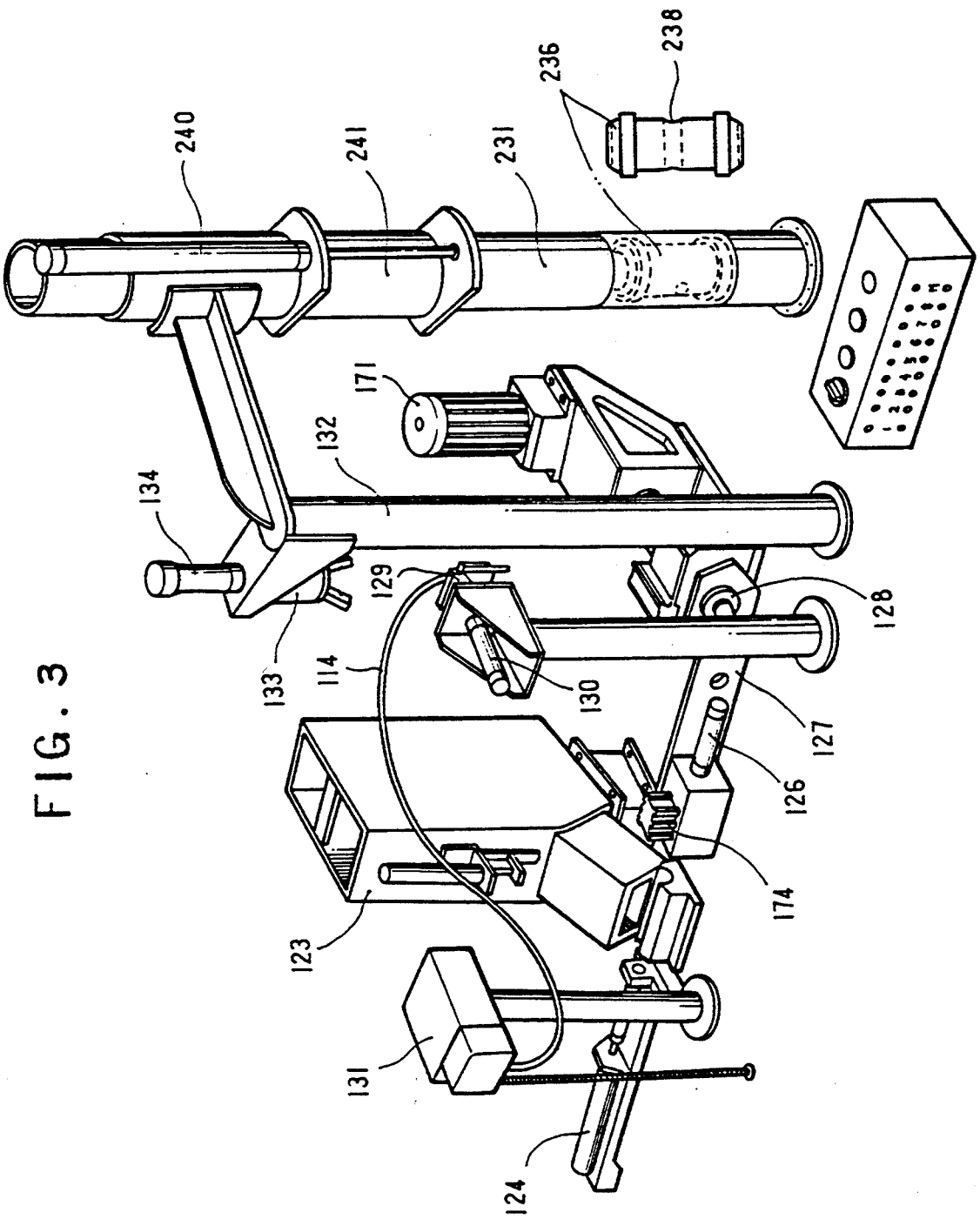
FIG. 3 is a perspective view showing the total constitution of the test sample taking section.

The automatic liquid sample analyzing apparatus according to the present invention includes a test sample taking section 100 which takes the test sample solution from a solution tank 1010 to put it into a sampling bottle. As shown in FIGS. 2 and 3, the test sample taking section 100 is installed adjacently to the production line solution tank 1010, and the test sample taking section 100 and the tank 1010 are connected with a pipe conduit 108 in a return form, in such a manner that the test sample solution should circulate by the action of a pump 109.

Figure 11:
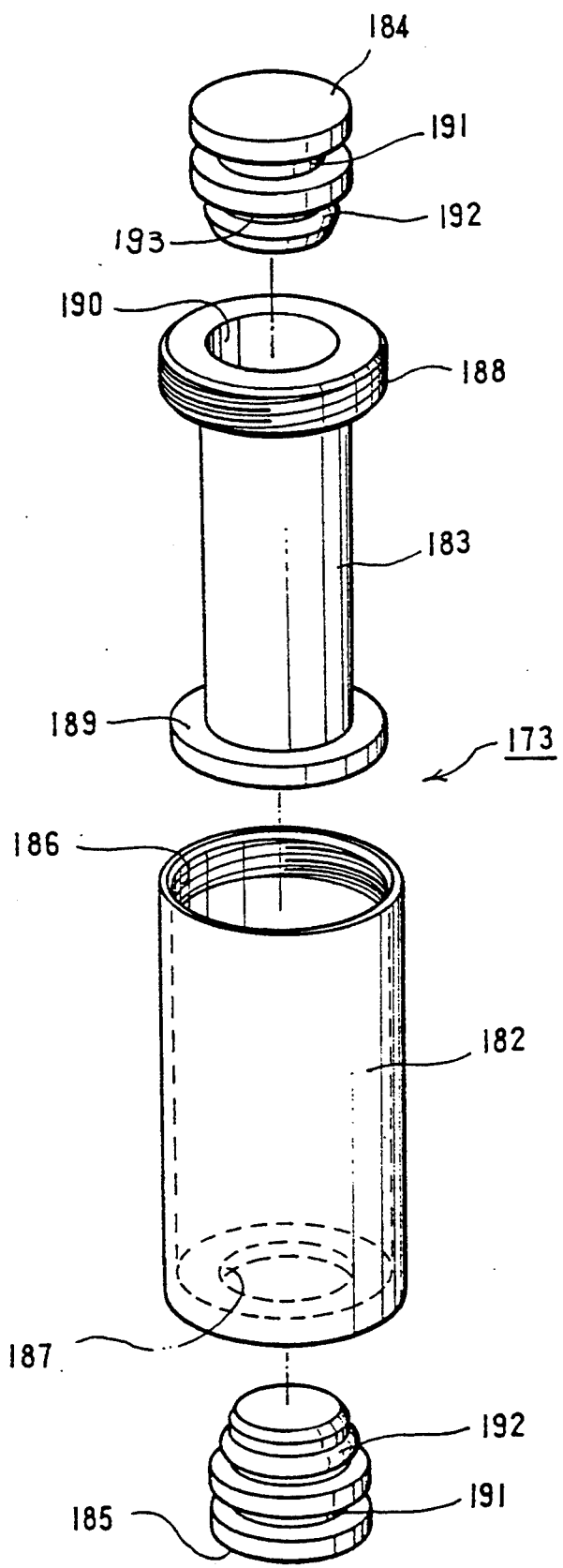
FIG. 11 is an exploded perspective view of the sampling bottle used in the present invention.
Figure 12:
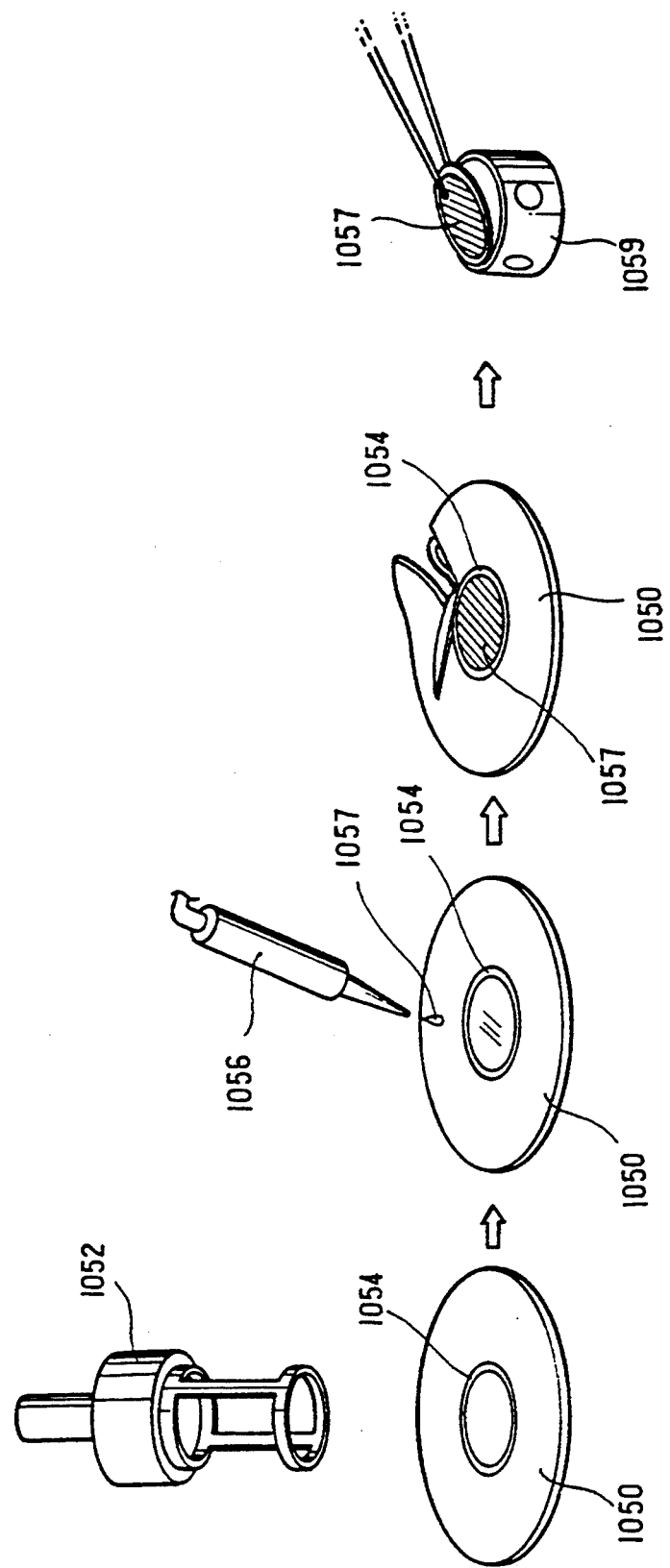
FIG. 12 illustrates the steps of the test sample preparing process based on the filtering method.
Figure 13:
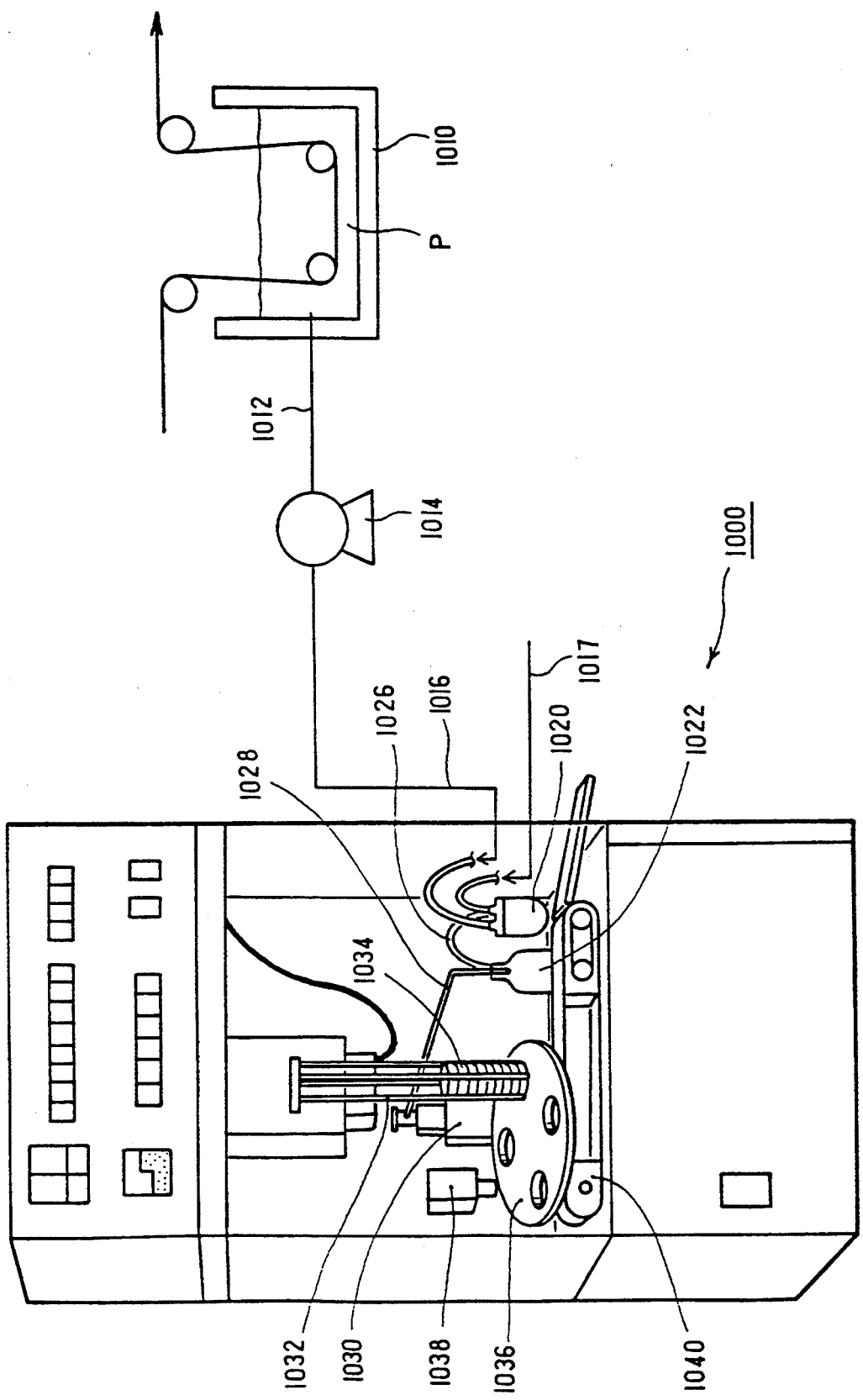
FIG. 13 illustrates the constitution of the conventional liquid test sample analyzing apparatus.

Further, a filter 106 is installed between the tank 1010 and the test sample taking section 100, so that the test sample solution to be analyzed should be circulated to and from the tank 1010 after passing through a test sample taking container 110 which is disposed below the test sample taking section 100. A supporting pole 111 is installed on the top of the test sample taking container 110 to secure pneumatic cylinders 112 and 113. A tube 114 is connected to an end of the pneumatic cylinder 113, so that the tube 114 can be moved to the left, right, up and down by the actuation of the pneumatic cylinders 112 and 113. A ceramic filter 115 is installed on the tip of the tube 114, so that the ceramic filter 115 should be able to move up and down within the containers 110 and 118 by passing through holes 117 and 119 which are formed respectively on the top of the test sample taking container 110 and on the top of a washing water storing container 118, whereby the ceramic filter 115 is submerged in a test sample solution 120 and a washing water 121. A sampling bottle storing barrel 123 is installed on a supporting plate 122, and a pneumatic cylinder 124 is installed at the left side of the sampling bottle storing barrel 123, while, at the right side of the sampling bottle storing barrel 123, there is formed sampling bottle inserting slot 125 and is installed a robot elbow 127 on which pneumatic cylinders 174 and 126 are installed. The pneumatic cylinders 174 and 126 are positioned respectively at a side and above the sampling bottle inserting slot 125. As shown in FIG. 3, the robot elbow 127 performs pivoting movements by 90° around a pivoting shaft 128 by a motor 171. On the right leading end, there is installed a pneumatic cylinder 130 on which a tube securing unit 129 is formed, and the tube 114 is fixed to the tube securing unit 129 in such a manner that it should be connected to an interlocking pump 131. Meanwhile, a supporting device 132 is installed at the right of the sampling bottle storing barrel 123, and a pneumatic cylinder 134 having a plug opening/closing device 133 is fixed on the top of the supporting device 132. Further, as shown in FIG. 11 the sampling bottle 173 into which the test sample solution is filled from the test sample container 110 through the tube 114 by the action of the interlocking pump 131 consists of an outer shell 182, an inner shell 183, and upper and lower plugs 184 and 185.

The outer shell 182 is provided with female threads on the upper inner circumference thereof, and is provided with a lower plug inserting hole 187 for inserting the lower plug 185 at the lower end thereof, thereby forming a hollow cylinder.

The inner shell 183 is provided with a male threads on the outer circumference thereof, and a stepped portion 189 is formed on the lower portion thereof. The inner shell 183 has a hollow portion 190 to contain the test sample solution, and its longitudinal section forms an I shaped contour, thereby forming a cylindrical form. The inner shell 183 is inserted into the outer shell 182 by coupling the female and male threads 186 and 188.

Further, annular grooves 191 are formed on the upper and lower plugs 184 and 185, and the plugs 184 and 185 are also respectively provided with an O ring insertion grooves 193 for inserting O rings 192 to seal off on the upper and lower ends thereof, whereby the upper and lower plugs 184 and 185 are inserted into the upper and lower ends of the inner shell 183. The inner and outer shells 182 and 183 are made of a plastic material which is low in its thermal conductivity and strong against acid solutions. The inner shell 183 which has an I shaped longitudinal section is inserted into the outer shell 182, and the female threads 186 of the outer shell 182 are coupled with the males threads 188 of the of the inner shell 183, thereby installing the inner shell 183 into the outer shell 182.

The lower plug insertion hole 187 which is formed on the bottom of the outer shell 182 and the upper hole 190 which is formed on the top of the inner shell 183 are press-fitted with the lower and upper plugs 185 and 184 on which the O ring is fitted, whereby the test sample solution contained in the hollow interior 190 is prevented from being leaked.

Particularly, there is formed an air layer between the outer shell 182 and the inner shell 183, so that the temperature of the test samples contained within the inner shell 183 should be prevented from being dropped. Further, the inner shell 183 is provided with the upper and lower plugs 184 and 185 having respectively an annular grooves 191, so that the plugs 184 and 185 can be easily attached and detached to and from the inner shell 183.

Figure 4A:
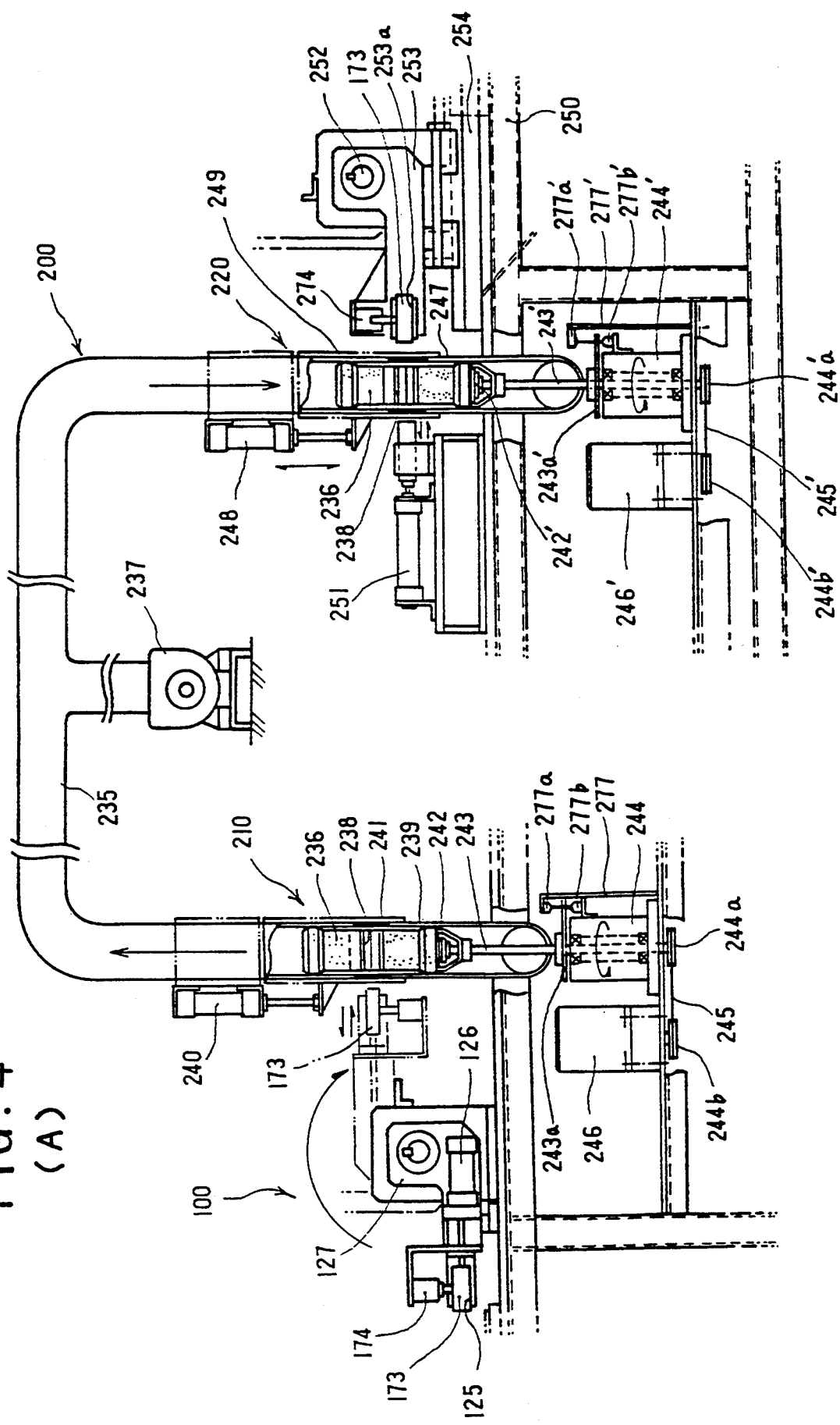
FIG. 4A is an enlarged sectional view showing the total constitution of the test sample carrying section of FIG. 2.
Figure 4:
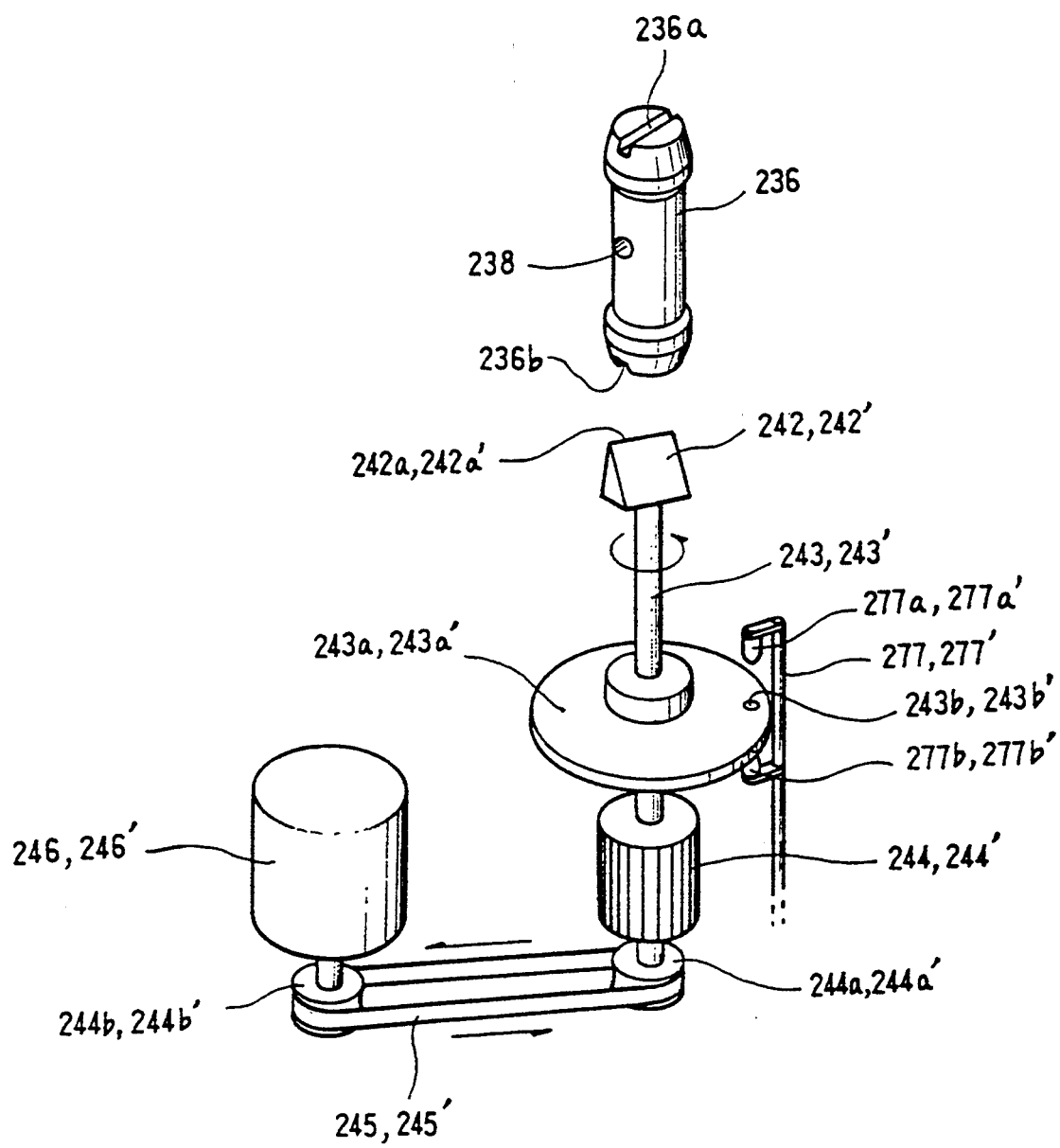
FIG. 4B is an enlarged perspective view showing a light irradiating device, a light receiving device and a rotary disc which are provided in the test sample carrying section.
Figure 5:
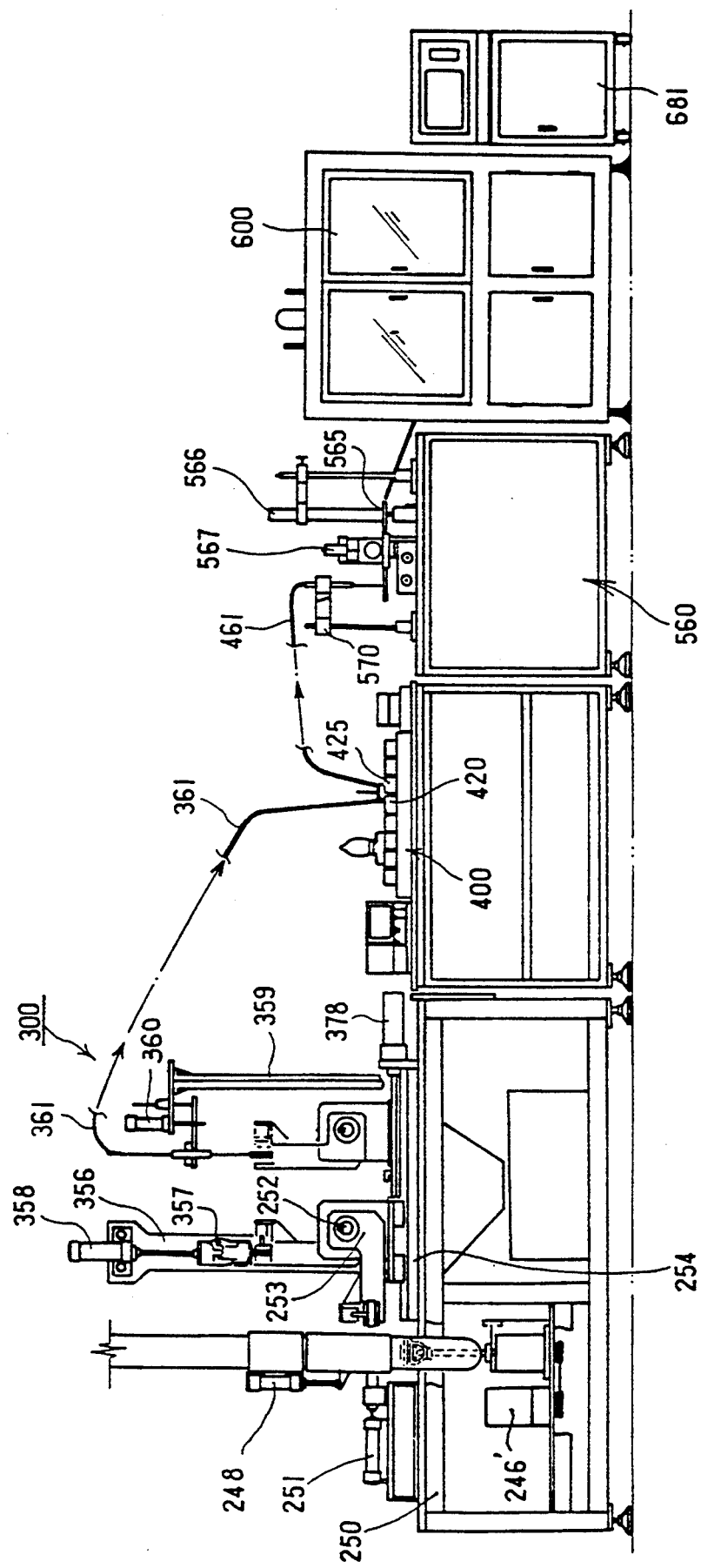
FIG. 5 is a frontal view showing the constitutions of the test sample readying section, the test sample pre-treating section, the filtered test sample preparing section and the analyzer according to the present invention.
Figure 6:
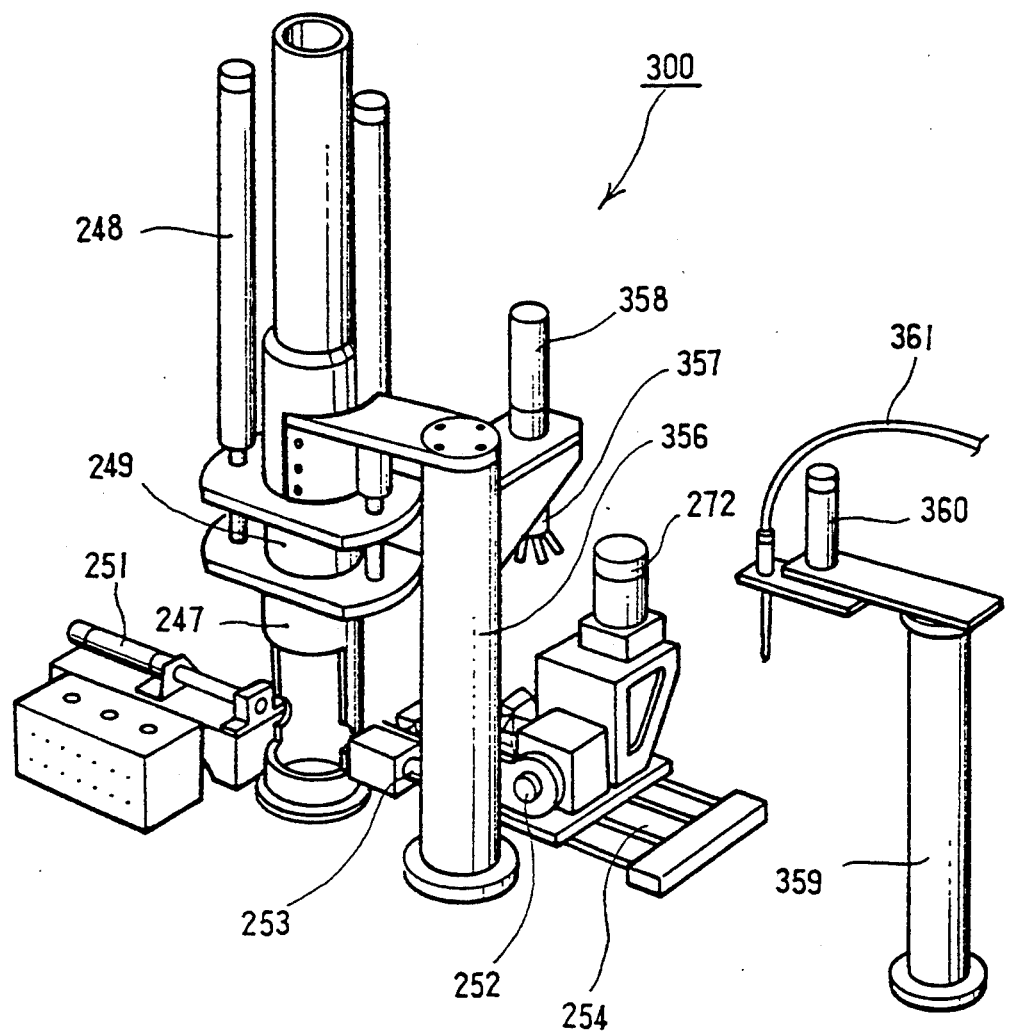
FIG. 6 is an external perspective view showing the total constitution of the test sample readying section of FIG. 5.

A test sample carrying section 200 is positioned adjacently to the test sample taking section 100, and automatically carries the test sample to a test sample readying section 300. As shown in FIG. 4, the test sample carrying section 200 includes: a starting terminal 210 installed on the test sample taking section 100; an arrival terminal 220 installed in the test sample readying section 300 of an analyzing room (not shown); an air carrying tube 235 for interconnecting the terminals 210 and 220; a carrying device 236 for loading the test sample; and a compressor 237 for producing an air pressure to carry the carrying device 236 through the air carrying tube 235. Within the air carrying tube 235 near the starting terminal 210, the carrying device 236 is provided with a hole 238 for loading the sampling bottle. On the top and bottom of the carrying device 236, there are formed V shaped recesses 236a and 236b. An inner tube 239 around the hole 238 of the carrying device 236 is cut away, and there is installed an outer tube 241 which is connected to a pneumatic cylinder 240, so that the outer tube 241 should be able to move up and down. On the lower end of the carrying device 236, a pad 242 is installed to connect it to a rotary rod 243, on the tip of which there is fixed a pulley 244a. Then it is connected through a belt 245 to a motor 246, so that when the motor 246 revolves, the rotary rod 243 should be rotated.

In the arrival terminal 220, when the carrying device 236 arrives, a part of the inner tube 247 around the hole 238 of the carrying device 236 is cut away, and there is installed an outer tube 249 which is connected to the pneumatic cylinder 248 which is fixed on the air carrying tube 235. The outer tube 249 is made to move up and down by the actuation of the pneumatic cylinder 248, while a pad 242' is installed within the inner tube 247 where the carrying device 236 arrives. A rotary rod 243' is connected to the bottom of the pad 242', and, on the end of the rotary rod 243', there is fixed a pulley 244a' which is connected through a belt 245' to a motor 246', so that the rotary rod 243' can be rotated when the motor 246' is driven.

A pneumatic cylinder 251 is installed upon a supporting plate 250 in such a manner that it should be aligned with the hole 238 of the carrying device 236. On the opposite side, there is installed a robot elbow 253 which is capable of pivoting by 90° clockwise around a pivoting shaft 252. Within the robot elbow 253, there is formed a sampling bottle inserting slot 253a. Above the sampling bottle inserting slot 253a of the robot elbow 253, there is installed a pneumatic cylinder 274 for press-fitting the sampling bottle 173, while a rail 254 which is provided under the robot elbow 253 is connected to the test sample readying section 300.

Meanwhile, as shown in FIG. 4, the carrying device 236 which carries the sampling bottle 173 within the air carrying tube 235 has an outside diameter corresponding to the inside diameter of the air carrying tube 235. Therefore, the carrying device 236 moves between the starting terminal 210 and the arrival terminal 220 by the actuation of the compressor 237.

Referring to FIG. 4, descriptions will be made as to how the carrying device 236 which is rotated by the motors 246 and 246' is disposed in such a manner that its central hole 238 is positioned in the lengthwise direction of the robot elbow 127 and 253.

That is, the pads 242 and 242' on which the carrying device 236 is positioned respectively have shaped inserting portions 242a and 242a' which are inserted into the upper and lower recesses 236a and 236b. The rotary rods 243 and 243' extend from the lower portions of the pads 242 and 242', and the rotary rods 243 and 243' have rotary discs 243a and 243a' in an integral form, while the discs are fitted with ball bearings 244 and 244' and are connected to pulleys 244a and 244a'. Further, the rotary discs 243a and 243a' are provided with holes 243b and 243b', and at a side of them, there are upstood supporting poles 277 and 277'. The supporting poles 277 and 277' are provided with light irradiating devices 277a and 277a' and light receiving devices 277b and 277b' which are opposingly facing each other, so that holes 243b and 243b' of the rotary discs 243a and 243a' can be detected. The light irradiating and receiving devices 277a, 277a', 277b and 277b' are electrically connected to motors 246 and 246' so as to control the driving of the motors.

Meanwhile the test sample readying section 300 is provided with a pneumatic cylinder 358 to which a plug opening/closing device 357 is connected. The plug opening/closing device 357 is installed on the left rear side of the rail 254 to remove the plug of the sampling bottle 173, when the robot elbow 253 horizontally moves along the rail 254.

A pneumatic cylinder 360 is installed on the top of a supporting device 359 which is positioned at the right side of the rail 254, and then, a tube 361 which is connected to a test sample pre-treating section 400 is fixed.

Figure 8:
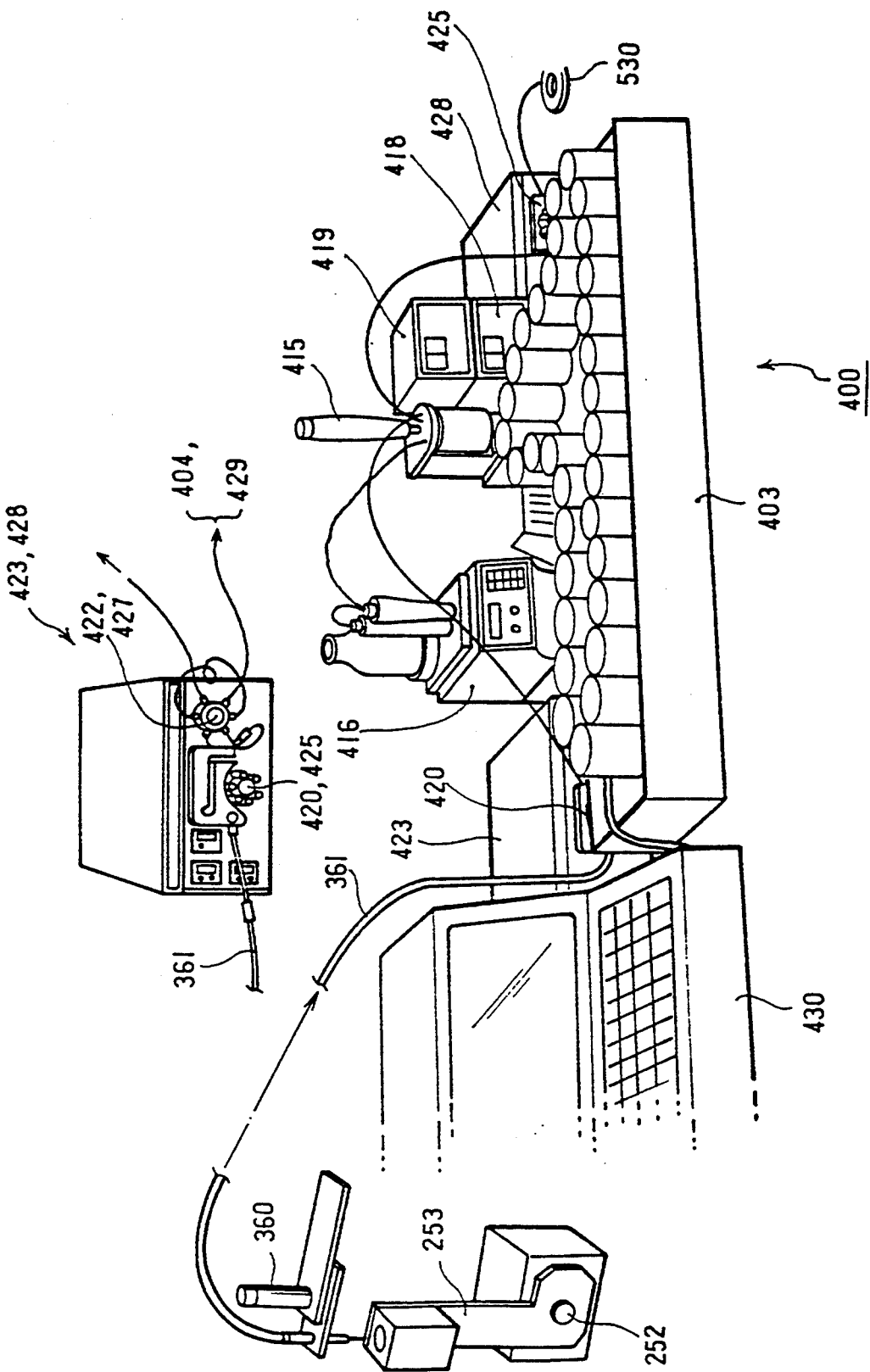
FIG. 8 is an external perspective view showing the total constitution of the test sample pre-treating section of FIG. 5.
Figure 9:
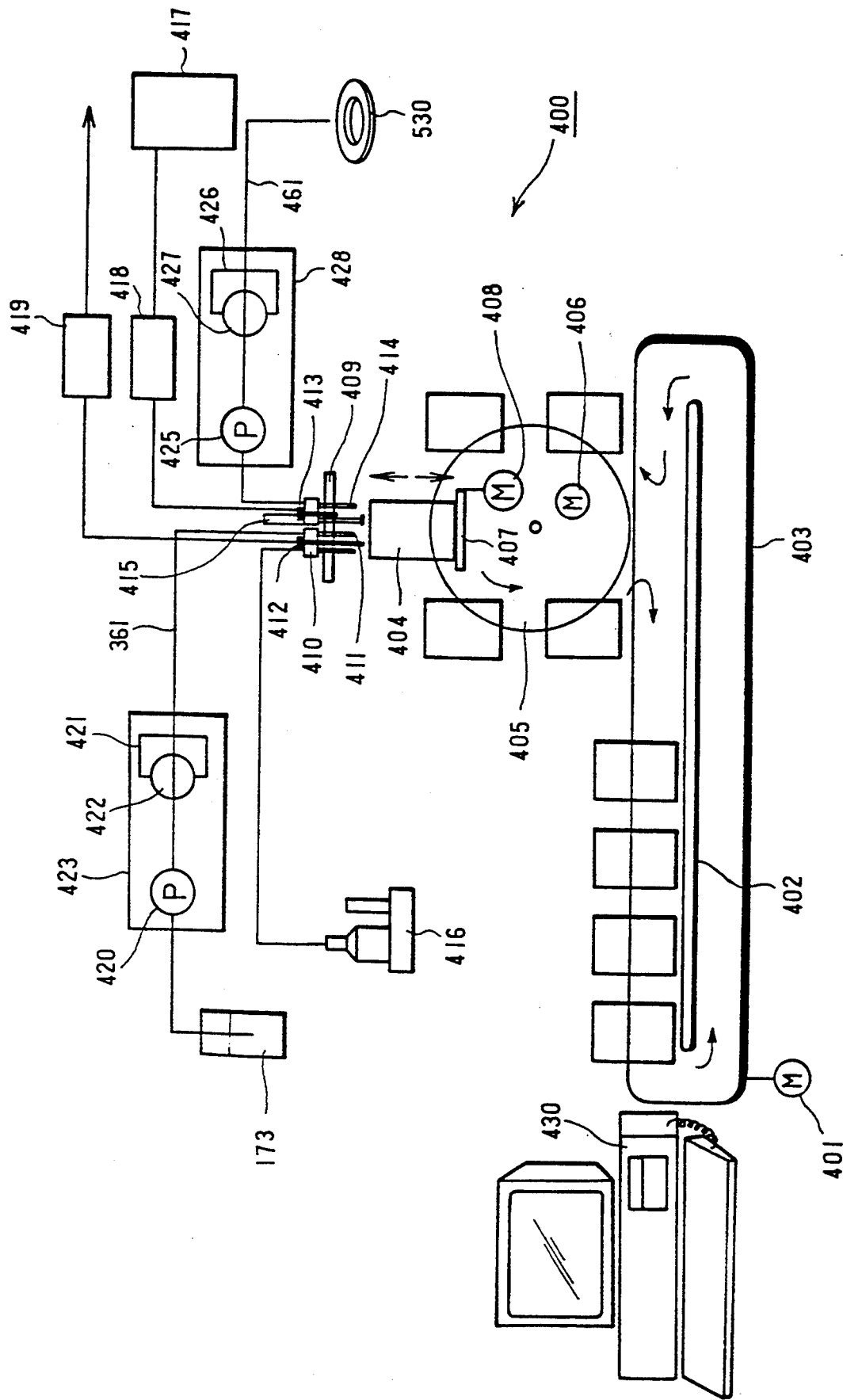
FIG. 9 is a schematic view showing the operation of the test sample pre-treating section.

As shown in FIGS. 8 and 9, the test sample pre-treating section 400 is provided with a circular rotary disc 405 which is capable of selecting and replacing 6 beakers. The disc 405 is installed at the right side of an automatic test sample exchanger 403 on which there is installed a conveyor belt 402 which is actuated by a motor 401. A motor 406 is installed at the center of the bottom of the circular rotary disc 405, so that the circular rotary disc 405 should be rotated by the motor 406. At the opposite lower end of the automatic test sample exchanger 403 of the circular rotary disc 405, there is installed a beaker supporting plate 407 which is connected to a motor 408, so that the beaker supporting plate 407 should move up and down by the action of the motor 408. A tube securing unit 409 is installed above the beaker supporting plate 407, while the tube securing unit 409 is connected to a distilled water injecting hole 410, a test sample injecting hole 411, a washing water injecting hole 413, a waste fluid discharge hole 412, a test sample taking hole 414, and an agitator 415.

The distilled water injecting hole 410 is connected to a distilled water ration supplier 416, and the washing water injecting hole 413 is connected through a pump 418 to a distilled water storing vessel 417, while the waste fluid discharge hole 412 is connected to a pump 419. The test sample injecting hole 411 is connected to a sampling unit 423 which includes an interlocked pump 420 and a 6-port valve 422 having a loop 421. As shown in FIG. 10, a certain amount of test sample solution is supplied from the sampling bottle 173 to the beaker 404 by the help of the interlocking pump 420 and the 6-port valve 422. The test sample taking hole 414 is connected to the sampling unit 428 which includes an interlocking pump 425 and a 6-port valve 427 having a loop 426, so that a certain amount of the test sample should be transferred to a droplet filtering paper 530 and various analyzers. Further, there is provided a computer 430 for automatically controlling the test sample pre-treating process.

Figure 7:
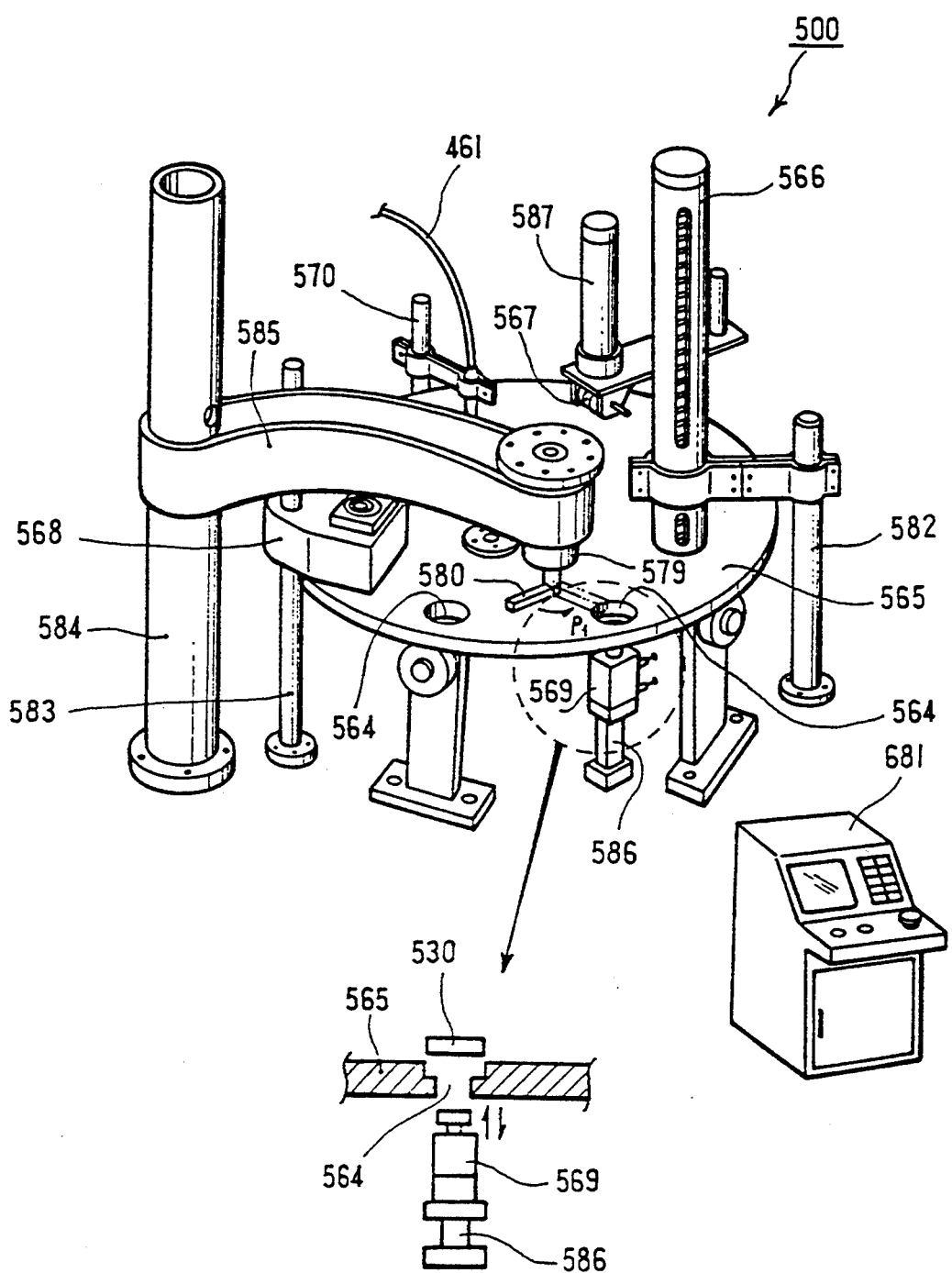
FIG. 7 is an external perspective view showing the total constitution of the filtered test sample preparing section of FIG. 5.

Meanwhile, a filtered paper test sample preparing section 500 which is installed downstream of the test sample pre-treating section 400 prepares the test sample by receiving the test sample through the tube 461 from the sampling unit 428. As shown in FIG. 7, a circular rotary plate 565 is installed at the center to be driven by a motor (not shown), and a filtering paper inserting holes 564 are formed on the rotary plate 565. At the right side of the circular rotary plate 565, there is provided a filtering paper storing device 566 in which a plurality of filtering papers 530 are stored. The open lower end of the filtering paper storing device 566 is aligned with the filtering paper inserting hole 564, and then, the filtering paper storing device 566 is secured by a filter paper storing device supporting pole 582.

At the left rear side of the filtering paper storing device 566, there is installed a marking device 567 which is capable of recording serial numbers on the filtering papers 530. Above the marking device 567, there is installed a pneumatic cylinder 587 which is capable of moving the filtering papers up and down. Above the circular rotary plate 565 and to left to the marking device 567, there is installed a tube supporting device 570 for securing the tube 461 which supplies the test sample after pre-treating the test sample by diluting or the like. The end of the tube 461 which is secured by the tube supporting device 570 is aligned with the center of the filtering paper insertion hole 564 which is formed on the circular rotary plate 565.

Further, upon the circular rotary plate 565 and at a position opposite to the filtering paper storing device 566, there is installed a drier 568 which includes a resistance coil and a blower (not shown) or which includes a blower and an infrared ray lamp. The drier 568 is secured by a drier supporting device 583.

In front of the drier 568, there is provided a cylindrical supporting device 584 on which a bar member 580 is secured. The bar member 580 is pivoted in the direction of an arrow mark P1 by a pneumatic cylinder 579 along a level between the drier 568 and the filter paper storing device 566. The pneumatic cylinder 579 is coupled with a connecting bar 585, so that the bar member 580 should be secured by the cylindrical supporting device 584 in such a manner as to be positioned above the filter paper insertion hole 564.

Below the circular rotary plate 565 and to the right of the bar member 580, there is installed a pneumatic cylinder 569 for discharging the filtering paper, and the pneumatic cylinder 569 is secured by a cylinder securing device 586 in such a manner that the pneumatic cylinder 569 should be aligned with the filtering paper insertion hole 564 of the circular rotary plate 565.

At the right side of the filtered test sample preparing section 500, there are installed analyzers 600 which consist of a fluorescent X-ray analyzer, an automatic dropper, an ultraviolet ray spectroscope, ion chromatography and the like. In the case of the X-ray analyzer, after passing through the filtered test sample preparing section 500, the droplet filtering paper with the test sample adhered thereon is carried into the fluorescent X-ray analyzer to be analyzed. In the case of the other analyzers, the test samples are directly transferred from the test sample pre-treating section 400 to the analyzers.

Reference code 681 indicates a computer which is capable of outputting various test results based on the analysis of the analyzers 600.

The apparatus of the present invention constituted as above will now be described as to its operations.

The test sample solution which is contained in the liquid sample storing tank 1010 circulates through the pipe conduit 108 continuously by the action of the pump 109. When this test sample solution passes the back filter 106, large particles in the form of floating materials are removed. When the operator activates the apparatus for performing a test of the sample, the pneumatic cylinder 124 which is positioned at the left side of the sampling bottle storing barrel 123 of the test sample taking section 100 supplies one of the sampling bottles from the sampling bottle storing barrel 123 to the sampling bottle insertion slot 125 of the robot elbow 127.

Upon supplying one of the sampling bottles 173, the robot elbow pivots clockwise by 90° around the pivoting shaft 128. Then the pneumatic cylinder 134 takes out the plug from the sampling bottle 173, and then, the pneumatic cylinder 130 is activated, so that the end of the tube 114 of the tube securing device 129 should be moved to above the sampling bottle 173, thereby becoming ready to take the test sample.

After becoming ready to take out the test sample as described above, the tube 114 is dipped into the test sample solution 120 by the action of the pneumatic cylinder 113. Then the interlocking pump 131 is activated, so that the test sample 120 should be filtered by the ceramic filter 115 for the second time. Then the test sample solution is transferred through the tube 114 to the sampling bottle 173 to be sampled.

After the completion of the sampling, the pneumatic cylinder 130 on which the tube securing device 129 is attached is restored to the original position. Then the pneumatic cylinder 134 on which the plug opening/closing device 133 is secured descends to close the upper plug 184 of the sampling bottle 173. Under this condition, the robot elbow 127 pivots by 90° clockwise around the pivoting shaft 128, and transfers the sampling bottle 173 to the automatic test sample carrying section 200 which will carry the sampling bottle to the ultimate destination.

When the sampling bottle 173 arrives at the starting terminal 210 of the test sample carrying section 200 which positioned at the left end of the air carrying tube 235, the pneumatic cylinder 240 which is attached on the air carrying tube 235 is activated, so that the outer tube 241 of the air carrying tube 235 should move up. Consequently, the hole 238 of the carrying device 236 which is inserted into the air carrying device 235 is made to be exposed to the outside. Then the pneumatic cylinder 174 of the robot elbow 127 loosens the tight state of the sampling bottle 173. Then the pneumatic cylinder 126 which is installed within the robot elbow 127 is activated to insert the sampling bottle 173 into the hole 238 of the carrying device 236. Then, upon completion of the loading of the sampling bottle 173, the pneumatic cylinder 240 which is attached on the air carrying tube is activated to make the outer tube 241 descend and to close the inner tube 239. Then the compressor 237 is activated to produce an air pressure to make the carrying device 236 fly to the destination, i.e., to the arrival terminal 220.

Then, if the carrying device 236 on which the sampling bottle 173 is loaded arrives at the destination, i.e., the arrival terminal 220, the insertion portion 242a' of the pad 242' is rotated by the motor 246'. Thus the insertion portion 242a' is inserted into the recess 236b which is formed on the bottom of the carrying device 236. Therefore, the carrying device 236 is rotated together with the pad 242'. Under this condition, light beams which are emitted from the light irradiating device 277a' are irradiated to the light receiving device 277b' through the hole 243b' of the rotary disc 243' which rotates together with the pad 242' by the motor 246'. Consequently, the light irradiating and receiving devices 277a' and 277b' makes the revolutions of the motor 246' stopped, so that the direction of the hole 238 of the carrying device 236 should be made to correspond with the lengthwise direction of the robot elbow 253.

Thus when the hole 238 of the carrying device 236 of the air carrying tube 235 is aligned with the pneumatic cylinder 251 (which is disposed on the opposite ends of the arrival terminal 220) and aligned with the inserting slot 253a of the robot elbow 253, the motor 246' automatically stops. Further, the pneumatic cylinder 248 which is attached on the air carrying tube 235 is activated to move the outer tube 249 upwardly. Further, the pneumatic cylinder 251 is activated, so that the sampling bottle 173 which is loaded in the hole 238 of the carrying device 236 is transferred to the inserting slot 253a of the robot elbow 253. Thus when the sampling bottle 173 is loaded into the robot elbow 253, the robot elbow 253 pivots clockwise around the pivoting shaft 252 to make the sampling bottle 173 upstand, and to transfer to the sampling bottle 173 to the test sample readying section 300.

The test sample readying section 300 keeps the sampling bottle 173 in the upright posture after the robot elbow 253 made so by being turned by 90°, and the plug opening/closing device 357 is positioned below. Under this condition, the plug opening/closing device 357 comes down by the action of the pneumatic cylinder 358 to open the upper plug 184 of the sampling bottle, and then, the plug opening/closing device 357 goes up to the original position. Under this condition, the pneumatic cylinder 378 is activated to move the robot elbow 253 horizontally to the right along the rail 254.

When the horizontal movement of the robot elbow 253 is completed, the pneumatic cylinder 360 which is installed on the top of the supporting device 359 is activated to lower the tube 361, so that the tip of the tube 361 should be dipped into the sampling bottle 173. The a certain amount of the test sample is taken by utilizing the ration pump 420 which is installed in the test sample pre-treating section 400. Then a test sample pre-treating process is carried out by diluting the sample, adding additives, and extracting particular ingredients.

This test sample pre-treating process will be described in further detail referring to FIG. 9. First, when the sampling bottle 173 with the test sample contained therein arrives, the pneumatic cylinder 360 of the supporting device 359 lowers the tube 361 to make it dipped into the sampling bottle 173. At the same time, the conveyor belt 402 of the automatic beaker exchanger 403 which constitutes the lower part of the test sample pre-treating section 400 is driven by the motor 401, so that the beakers mounted on the top thereof should be moved together. Then the circular rotary disc 405 which is disposed above the automatic beaker exchanger 403 is rotated by a certain angular degree by the motor 406. Then a new beaker 104 is transferred from the conveyor belt 402 of the automatic beaker exchanger 403 to the beaker supporting device 407. Thereafter, the motor 408 is activated to lift the beaker 404 to a certain height, i.e., to the lower portion of the tube supporting device 409. Then the interlocking pump 420 of the sampling unit 423 and the 6-port valve 422 positioned near the former are activated, so that a certain amount of the test sample should be transferred from the sampling bottle 173 to the beaker 404. Under this condition, as shown in FIG. 10, the 6-port valve 422 is activated to charge a certain amount of the test sample into the beaker 404.

Figure 10A:
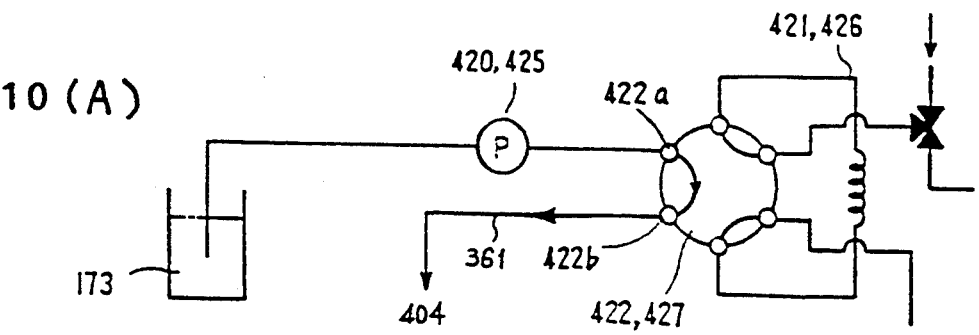
FIGS. 10A–10D illustrates the operating principle of the steps of a 6-port valve of the test sample pre-treating section of FIGS. 8 and 9.

As shown in FIG. 10A, when the interlocking pump 420 sucks in the test sample from the sampling bottle, first the test sample is discharged through the inlet port 422a and the discharge port 422b so as to be drained.

Figure 10B:
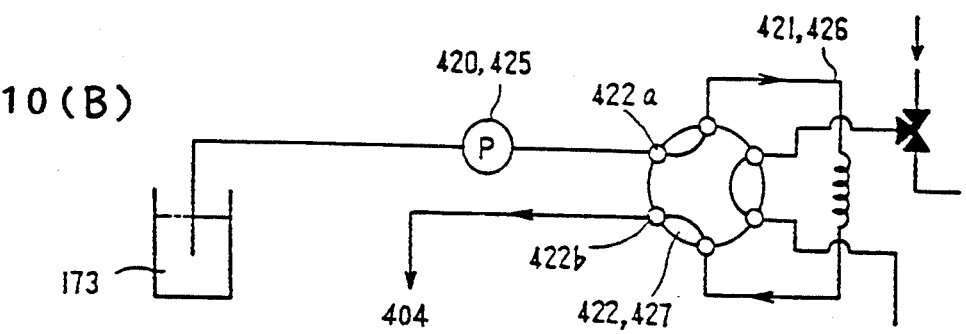

At the next step as shown in FIG. 10B, the inlet port 422a is connected to the tip of a round-about tube 421 to supply the test sample solution to the round-about tube 421. The discharge port 422b is connected to the round-about tube 421, so that the test sample should be discharged through the inlet port 422a, the round-about tube 421c and the discharge port 422b.

Figure 10C:
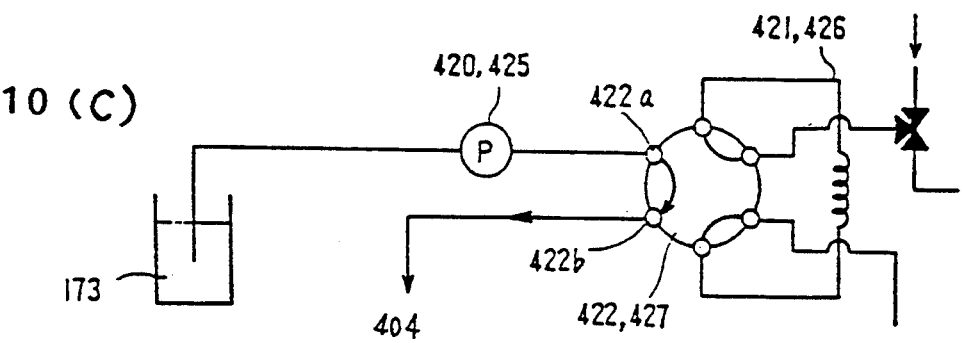

At the next step as shown in FIG. 10C, the inlet port 422a is connected to the discharge port 422b again, and the opposite ends of the round-about tube 421 are closed, so that a certain amount of the test sample should be stored within the round-about tube 421.

Figure 10D:
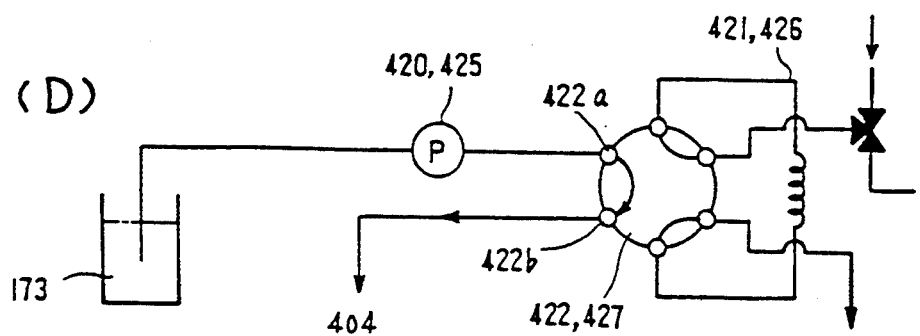

At the next step as shown in FIG. 10D, with the inlet port 422a and the discharge port 422b connected together, a compressed air is introduced through one end of the round-about tube 421, while the other end of the round-about tube 421 is opened and connected to the tube 361 leading to the beaker 404. Consequently, the test sample of the round-about tube 421 is transferred to the beaker 404 by the action of the compressed air. Such operation is repeated.

Thus certain amounts of the test samples are continuously taken by the 6-port valve 422. When a certain amount of the test sample is transferred from the sampling bottle to the beaker 404, the distilled water ration supply device 416 is activated to supply a certain amount of the distilled water through a distilled water inject hole 410 into the beaker 404. Then the agitator 415 is operated for a certain period of time to dilute the test sample in a certain ratio.

After the completion of the dilution, the 6-port valve 427 and the interlocking pump 425 of the sampling unit 428 are activated again, so that a certain amount of the test sample should be supplied to an analyzer, or that a certain amount of the test sample should be supplied to the droplet filtering paper 530 for a filtering paper analysis.

After the completion of the automatic injection of the test sample, the residue solution which remain within the beaker 404 is automatically discharged by the discharge pump 419. Then the washing water is supplied from the distilled water storing vessel 417 into the beaker 404 by the action of the pump 418. Then an agitation is carried out by means of the agitator 415, and then, the discharge pump 419 is activated to discharge the cleaning water. Thus the beaker is automatically washed, so that the beaker should be ready for the next round of the process. Such test sample pre-treating process is automatically carried out by using a computer 430 based on a computer program for meeting the timing.

After the completion of the test sample pre-treating process, the 6-port valve 427 and the pump 425 of the sampling unit 428 are activated, so that the test sample should be supplied to various analyzing instruments 600 to be analyzed by them.

Meanwhile, of the various analyzing instruments such as a fluorescent X-ray analyzer, an automatic dropping apparatus, an ultraviolet spectroscopy, an infrared spectroscopy and ion chromatography, if a fluorescent X-ray analyzer is to be used, then the filtered test sample preparing section 500 according to the present invention is activated simultaneously with the test sample pre-treating section 400.

As shown in FIG. 7, the filtered test sample preparing section 500 operates in the manner described below. That is, during the time when the test sample pre-treating section 400 carries out the pre-treating work, a central motor (not shown) is activated to turn the circular rotary plate 565 by a certain angular degree. Then a droplet filtering paper 530 is dropped from the filtering paper storing device 566 into the filtering paper insertion hole 564 which is formed on the circular rotary plate 565. Then the circular rotary plate 565 is turned by 90°, so that the droplet filtering paper 530 should be positioned below the marking device 567. When the droplet filtering paper 530 is positioned below the marking device 567, the marking device 567 marks a serial number on the margin of the droplet filtering paper 530, and then, the marking device 567 ascends. The marking device 567 marks different serial numbers on the incoming different filtering papers 530 by incrementing the number one by one.

After marking of the serial number, the droplet filtering paper 530 is moved to below the tube supporting device 570 by the action of the central motor in accordance with the rotation of the circular rotary plate 565, to be stopped there. Thus the filtering paper 530 waits until the test sample from the test sample pre-treating section 400 is dropped onto the center of the filtering paper 530. That is, the test sample which is diluted by a certain ratio by the test sample pre-treating section 400 is supplied through the tube 461 to be dropped onto the filtering paper 530. Then the circular rotary plate 565 is turned by 90°, so that the droplet filtering paper 530 should be positioned below the drier 568 to be dried by it for a certain period of time.

After the completion of the drying, the circular rotary plate 565 is rotated again, so that the droplet filtering paper 530 should be moved to above the discharge pneumatic cylinder 569. Then the filtering paper discharging pneumatic, cylinder 569 is activated to lift up the droplet filtering paper 530 to a certain height from the filtering paper insertion hole 564 which is formed on the circular rotary plate 565. Then the pneumatic cylinder 579 is activated to pivot the bar member 580, thereby pushing the left side of the droplet filtering paper 530. By the force of the bar member 580, the filtering paper 530 passes through a discharge hole (not shown) to depart from the filtered test sample preparing section 500. The filtering paper which has passed through the discharge hole is carried to the fluorescent X-ray analyzer of the analyzing instruments 600.

Meanwhile, the analyzing instruments 600 are provided with a computer 681 for analyzing the various ingredients of the test sample, and for outputting the analyzed results to the outside, thereby detecting the various ingredients of the test sample.

After the completion of the automatic sampling and analyzing, the pneumatic cylinder 248 which is attached on the arrival terminal 220 of the air carrying tube 235 is activated to lower the outer tube 249 and to close the cut-off inner tube 247. Then air is introduced to the pad 242' to release the fixed state of the carrying device 236, and then, the compressor 237 is activated to carry the carrying device 236 to the starting terminal 210 by means of the air pressure. When the carrying device 236 arrives at the starting terminal 210, the pad 242 secures the carrying device 236 like at the arrival terminal 220. Then the motor 246 is activated to rotate the rotary rod 243 which is attached on the pulley 244a, so that the carrying device 236 should turn together. Under this condition, the light irradiating and receiving devices 277a and 277b are used, so that the motor 246 should automatically stop when the hole 238 of the carrying device 236 within the air carrying tube 235 is aligned on a straight line with the pneumatic cylinders 126 of the opposite ends and the insertion hole 125 of the robot elbow 127, thereby readying for the carrying of the test sample for the next test.

According to the automatic liquid test sample analyzing apparatus according to the present invention as described above, if it is used for analyzing the various ingredients of the liquid test sample, the analysis is carried out in the on-line real time so as to be speedily fed back. Therefore, a strict supervision of the test sample solution can be carried out, thereby obtaining the improvement of the quality of the products. Further, the test sample solution is circulated, so that the blocking of the conduit should be prevented, and the ingredient difference between the test sample of the test sample storing tank and that of the conduit can be avoided. Further, even under an atmosphere in which the corroding effect is severe, the corrosion of the analyzing instruments can be avoided, because only the automatic test sample taking section 100 is placed on the site of the production line, and the test sample is carried to an analyzing room. Further, even in the case where there are many kinds of test samples and many storing tanks, only the automatic test sample taking section is added in a plural form without adding any other facility. The plurality of the test sample taking sections have only to be connected to the test sample carrying section 200. Therefore, the expansion of the facility is easy.

What is claimed is:

1. A liquid test sample analyzing apparatus comprising:
   a test sample taking section (100) for taking a test sample from a liquid test sample solution (120) storing tank (1010) of a production line and for filling the taken test sample into a sampling bottle (173);
   a test sample carrying section (200) for carrying said sampling bottle (173) containing said test sample from said test sample taking section (100) to an analyzing room;
   a test sample readying section (300) for opening or closing an upper plug (184) of said sampling bottle (173) from said test sample carrying section (200) including means to draw said test sample;
   a test sample pre-treating section (400) including means for drawing said test sample solution from said test sample readying section (300) to dilute, or to add additives or extract a selected amount of test sample solution;
   a filtered test sampling preparing section (500) for preparing said test sample from said test sample pre-treating section (400), wherein solid materials from said test sample solution are deposited on a filtering paper (530); and
   analyzing instruments (600) for analyzing said test sample supplied from said test sample pre-treating section (400) and said filtered test sample preparing section (500), and wherein said test sample taking section (100) includes:
   a pipe conduit (108) return-connected to said liquid test sample storing tank (1010);
   a pump (109) and a filter (106) installed at intermediate positions of said pipe conduit (108) for filtering the test sample solution;
   a test sample taking container (110) and a washing water storing container (118) installed below said test sample taking section (100);
   pneumatic cylinders (112) and (113) secured on a supporting device (111) of said test sample taking container (110) for moving up and down a tube (114), and a filter (115) installed on said tube (114) for filtering the test sample solution a second time;
   a sampling bottle storing barrel (123) installed on the middle of the top of a supporting plate (122);
   a pneumatic cylinder (124) installed at a first side of said sampling bottle storing barrel (123);
   a robot elbow (127) installed at a second side of said sampling bottle storing barrel (123), and for securing said sampling bottle (173) by means of a sampling bottle insertion slot (125) and a pneumatic cylinder (174);
   a pneumatic cylinder (130) connected to a tube securing unit (129) and installed above said supporting plate (122);
   a pneumatic cylinder (134) having a plug opening/closing device (133) and installed upon a supporting device (132); and
   an interlocking pump (131) installed at an intermediate position of said tube (114),
   whereby the blocking of said pipe conduit (108) due to the precipitation of the test sample solution is prevented, and the taking of said test sample is automatically carried out.

2. The automatic liquid sample analyzing apparatus as claimed in claim 1, wherein said test sample carrying section (200) includes:
   a carrying device (236) having a through hole (238) for loading said sampling bottle (173) within an air carrying tube (235), said sampling bottle (173) containing said test sample solution (120);
   a compressor (237) for moving said carrying device (236) within said air carrying tube (235);
   a starting terminal (210) formed at an end of said air carrying tube (235), an inner tube (239) of said starting terminal (210) being cut away around the hole (238) of said carrying device (236);
   an outer tube (241) coupled with said inner tube (239) in such a manner as to be moved up and down, to permit said cut away portion to be opened and closed;
   said hole (238) of said carrying device (236) being so positioned as to load said sampling bottle (173) from said robot elbow (127) of said test sample taking section (100) by activation of a pneumatic cylinder (126);
   an arrival terminal (220) formed at the other end of said air carrying tube (235), an inner tube (247) of said arrival terminal (220) being partly cut away for settling said carrying device (236);
   an outer tube (249) coupled with said inner tube (247) in such a manner as to be moved up and down by a pneumatic cylinder (248), so as for said cut portion of said inner tube (247) to be opened and closed;
   a pneumatic cylinder (251) installed at a first side of said arrival terminal (220) for removing said sampling bottle (173) from said carrying device (236);
   a pneumatic cylinder (274) installed at a second side of said arrival terminal (220) side for securing said sampling bottle (173), and a robot elbow (253) installed also at the second side pivotally around a pivoting shaft (252), said robot elbow (253) being movable horizontally along a rail (254);
   pads (242) and (242') interconnected with rotary rods (243) and (243'), and installed in a lower portion of said inner tubes (239) and (247) of the opposite ends of said air carrying tube (235);
   motors (246) and (246') respectively connected through belts (245) and (245') and pulleys (244a), (244a'), (244b) and (244b') to said rotary rod (243) and (243'); and light irradiating devices (277a) and (277a') and light receiving devices (277b), and (277b') installed below said rotary rod (243) and (243 ') for controlling said motors (246) and (246').

3. The automatic liquid sample analyzing apparatus as claimed in claim 2, wherein said light irradiating and light receiving devices (277a), (277a'), (277b), (277b') detect light beams through holes (243b) and (243b') of rotary discs (243a) and (243a') formed integrally with said rotary rod (243) and (243'), and stop the operations of said motors (246) and (246'), whereby said hole (238) of said carrying device (236) is aligned with insertion slots (125) and (253a) of said robot elbow (127) and (253).

4. The automatic liquid sample analyzing apparatus as claimed in claim 1, wherein said test sample readying section (300) includes:

a pneumatic cylinder (378) for moving a robot elbow (253) of said test sample carrying section (200) horizontally along a rail (254);

a plug opening/closing device (357) for taking out said upper plug (184) from said sampling bottle (173), in a state with said sampling bottle (173) secured by said robot elbow (253);

said plug opening/closing device (357) being moved up and down by a pneumatic cylinder (358) installed on a supporting device (356); and a pneumatic cylinder (360) installed on a supporting device (359) and at a side of said supporting device (356) for dipping the end of a tube (361) into said sampling bottle (173) after the opening of the upper plug of said sampling bottle (173).

5. The automatic liquid sample analyzing apparatus as claimed in claim 1, wherein said sampling bottle (173) includes:

an outer shell (182) including female threads on an upper inner circumferential portion thereof, and a lower plug insertion hole (187) formed on a bottom thereof and for inserting a lower plug (185);

an inner shell (183) including male threads (188) formed on an upper outer circumferential portion thereof, a stepped portion formed below said male threads, a hollow space (190) for containing the test sample, and an I shaped longitudinal section for being coupled with said outer shell (182); and said upper and lower plugs (184) and (185) having annular grooves (191), and grooves (193) for fitting an O ring (192).

6. The automatic liquid sample analyzing apparatus as claimed in claim 1, wherein said test sample pre-treating section (400) includes:

a circular rotary disc (405) installed above an automatic test sample exchanger (403) with a plurality of beakers (404) loaded thereon, and for replacing said beakers (404) in an orderly manner upon a supporting plate (407);

an interlocking pump (420) and a 6-port valve (421) for supplying said test sample solution (120) to said beaker (404);

a ration supplying device (416) for supplying an amount of distilled water into said beaker (404) to dilute the test sample;

a distilled water storing vessel (417) and a pump (418) for supplying a washing water to said beaker (404);

a pump (419) for discharging a waste test sample solution from said beaker (404);

an agitator (415) for agitating said beaker (404) with the test sample contained; and a computer for controlling the diluting of the test sample, or the adding or extracting a selected amount of test sample solution.

7. The automatic liquid sample analyzing apparatus as claimed in claim 1, wherein said filtered test sample preparing section (500) includes:

a circular rotary plate (565) rotated by a motor and a plurality of filtering paper inserting holes;

a filtering paper storing device (566) for settling droplet filtering papers (530) into insertion holes (564) in a sequential manner;

a marking device (567) moved up and down by a pneumatic cylinder (587) for marking serial numbers on said droplet filtering papers (530) of said insertion holes (564);

a tube supporting device (570) for securing a tube (461) for dropping drops of the test sample onto said droplet filtering papers (530) of said insertion hole (564);

a dryer (568) installed at a side of said tube supporting device (570) for heat-drying said droplet filtering papers (530) with the test sample adhered thereon;

a cylindrical supporting device (584) installed at an intermediate position between said dryer (568) and said filtering paper storing device (566), and having a bar member (580) for pushing said droplet filtering paper (530); and a filtering paper discharging pneumatic cylinder (569) installed below said circular rotary plate (565) for lifting the droplet filtering papers (530) through said insertion hole (564).

8. The automatic liquid sample analyzing apparatus as claimed in claim 1, wherein said analyzing instrument (600) includes an analyzing instrument selected from the group consisting of: a fluorescent X-ray analyzer, an automatic droplet dropping apparatus, an ultraviolet spectroscopy apparatus, an infrared spectroscopy apparatus, an ion chromatography apparatus, and further includes a computer (68) for outputting the test data for the test sample solution (120).

9. The automatic liquid sample analyzing apparatus as claimed in claim 2, wherein said sampling bottle (173) includes:

an outer shell (182) including female threads on an upper inner circumferential portion thereof, and a lower plug insertion hole (187) formed on a bottom thereof and for inserting a lower plug (185);

an inner shell (183) including male threads (188) formed on an upper outer circumferential portion thereof, a stepped portion formed below said male threads, a hollow space (190) for containing the test sample, and an I shaped longitudinal section for being coupled with said outer shell (182); and said upper and lower plugs (184) and (185) having annular grooves (191), and grooves (193) for fitting an O ring (192).

10. The automatic liquid sample analyzing apparatus as claimed in claim 8 wherein the analyzing instrument (600) is a fluorescent X-ray analyzer and wherein the test sample solution (120) is supplied through said filtering paper (530) of said filtered test sample preparing section (500).

11. The automatic liquid sample analyzing apparatus as claimed in claim 8 wherein the analyzing instrument (600) is one selected from the group consisting of the automatic droplet dropping apparatus, the ultraviolet spectroscopy apparatus, the infrared spectroscopy apparatus and the ion chromatography apparatus and wherein the test sample solution (120) is supplied from said test sample pre-treating section (400).

* * * * *

UNITED STATES PATENT AND TRADEMARK OFFICE
CERTIFICATE OF CORRECTION

PATENT NO. : 5,441,699
DATED : August 15, 1995
INVENTOR(S) : Jai-Choon So, Hae-Il Kwak, Kyu-Hae Hwang, Yong-Hwan Cho, Ki-Jin Eom and Sa-Ryong Pack It is certified that error appears in the above-indentified patent and that said Letters Patent is hereby corrected as shown below:

Abstract Line 4 "is" should read --are--.

Column 1 Line 68 "electrolyte p" should read --electrolyte P--.

Column 5 Line 14 before "male" delete "a".

Column 5 Line 24 before "O ring" delete "an".

Column 5 Line 34 "males" should read --male--.

Column 5 Line 34 delete "of the" (second occurrence).

Column 5 Line 49 after "respectively" delete "an".

Column 6 Line 52 after "have" insert --^--.

Column 7 Line 60 after "and" delete "a".

Column 8 Line 7 "to left to" should read --to the left of--.

Column 8 Line 50 after "capable" insert --of--.

Column 9 Line 27 after "which" insert --is--.

Column 9 Line 59 "makes" should read --make--.

UNITED STATES PATENT AND TRADEMARK OFFICE
CERTIFICATE OF CORRECTION

PATENT NO. : 5,441,699
DATED : August 15, 1995
INVENTOR(S) : Jai-Choon So, Hae-Il Kwak, Kyu-Hae Hwang, Yong-Hwan Cho, Ki-Jin Eom and Sa-Ryong Pack It is certified that error appears in the above-indentified patent and that said Letters Patent is hereby corrected as shown below:

Column 10 Line 29 "The a" should read --Then a--.

Column 11 Line 35 "remain" should read --remains--.

Column 12 Lines 29-30 "discharging pneumatic," should read --discharge pneumatic--.

Claim 1 Lines 28-30 Column 13 "taking a test sample from a liquid test sample solution (120) storing tank (1010)" should read --taking a test sample solution (120) from a liquid test sample storing tank (1010)--..

Signed and Sealed this

Twenty-eighth Day of May, 1996

Attest:

BRUCE LEHMAN

*Attesting Officer*  *Commissioner of Patents and Trademarks*